United States Patent
Verte

(10) Patent No.: US 12,004,522 B2
(45) Date of Patent: Jun. 11, 2024

(54) SOURDOUGH PRODUCT

(71) Applicant: PURATOS NV, Groot-Bijgaarden (BE)

(72) Inventor: Fabienne Verte, Destelbergen (BE)

(73) Assignee: PURATOS NV, Groot-Bijgaarden (BE)

( * ) Notice: Subject to any disclaimer, the term of this patent is extended or adjusted under 35 U.S.C. 154(b) by 432 days.

(21) Appl. No.: 17/415,247

(22) PCT Filed: Jan. 10, 2020

(86) PCT No.: PCT/EP2020/050595
§ 371 (c)(1),
(2) Date: Jun. 17, 2021

(87) PCT Pub. No.: WO2020/144361
PCT Pub. Date: Jul. 16, 2020

(65) Prior Publication Data
US 2022/0053781 A1 Feb. 24, 2022

(30) Foreign Application Priority Data
Jan. 11, 2019 (BE) .................. 2019/5017

(51) Int. Cl.
A21D 8/04 (2006.01)
A21D 10/00 (2006.01)
C12R 1/145 (2006.01)

(52) U.S. Cl.
CPC .......... *A21D 8/045* (2013.01); *A21D 10/002* (2013.01); *C12R 2001/145* (2021.05)

(58) Field of Classification Search
CPC ...... A21D 8/045; A21D 10/002; C12N 1/205; C12R 2001/145
USPC ........................................................ 426/18
See application file for complete search history.

(56) References Cited

PUBLICATIONS

Koy https://pearl.plymouth.ac.uk/handle/10026.1/9828 Thesis Aug. 2017 "Lactic acid bacteria as bio-preservatives in bakery—Role of sourdough systems in the quality, safety and shelf life of bread" University of Plymouth UK (Year: 2017).*
European Patent Office, "Communication," issued in European Patent Application No. 20 700 035.7, which is a counterpart to U.S. Appl. No. 17/415,247, dated Aug. 2, 2022, 8 pages.
Maria De Angelis et al., "Wholemeal wheat flours drive the microbiome and functional features of wheat sourdoughs," IInternational Journal of Food Microbiology, Elsevier BV, NL, vol. 302, 2019, pp. 35-46, XP085710276, doi: 10.1016/j.ijfoodmicro.2018.08.009.
Jian Ding et al., "Electron receptor addition enhances butanol synthesis in ABE fermentation by Clostridium acetobutylicum," Bioresource Technology, Elsevier, Amsterdam, NL, vol. 247, 2018, pp. 1201-1205, XP085298860, DOI: 10.1016/j.biortech.2017.09.010.
International Search Report dated May 6, 2020 in connection with PCT International Patent Application No. PCT/EP2020/050595.
Written Opinion of the International Search Authority dated May 6, 2020 in connection with PCT International Patent Application No. PCT/EP2020/050595.
Notification of Transmittal of the International Preliminary Report on Patentability dated Feb. 3, 2021 in connection with PCT International Patent Application No. PCT/EP2020/050595.
Menezes L A A et al: "Sourdough bacterial dynamics revealed by metagenomic analysis in Brazil", Food Microbiology, vol. 85, Aug. 14, 2019 (Aug. 14, 2019), 11 pages, XP085809271.
Rupesh S. Chavan et al: "Sourdough Technology—A Traditional Way for Wholesome Foods: A Review", Comprehensive Reviews in Food Science and Food Safety, vol. 10, No. 3, May 6, 2011 (May 6, 2011), pp. 169-182, XP055166864.
Ganzle Michael G Ed—Poutanen Kaisa et al: "Enzymatic and bacterial conversions during sourdough fermentation", Food Microbiology, vol. 37, Apr. 25, 2013 (Apr. 25, 2013), pp. 2-10, XP028770931.
Ye Ni et al: "Butanol Production from Cane Molasses by Clostridium saccharobutylicum DSM 13864: Batch and Semicontinuous Fermentation", Applied Biochemistry and Biotechnology, vol. 166, No. 8, Feb. 24, 2012 (Feb. 24, 2012), pp. 1896-1907, XP055615557.

\* cited by examiner

*Primary Examiner* — Subbalakshmi Prakash
(74) *Attorney, Agent, or Firm* — Amster, Rothstein & Ebenstein LLP

(57) ABSTRACT

The present invention provides products and methods for improving the tolerance of a dough in bakery and patisserie products. More specifically it provides sourdough products obtained through the fermentation of cereals by specific strains of bacteria. The products obtained by using said sourdough products are characterized by having a strengthened dough resulting in bakery and patisserie products with improved physical properties and taste.

28 Claims, No Drawings

SOURDOUGH PRODUCT

CROSS-REFERENCE TO RELATED APPLICATIONS

This application is a U.S. national stage entry under 35 U.S.C. § 371 of PCT International Patent Application No. PCT/EP2020/050595, filed Jan. 10, 2020, which claims priority to Belgian Patent Application No. 2019/5017, filed Jan. 11, 2019, the contents of each of which are incorporated herein by reference in their entirety.

FIELD OF THE INVENTION

The present invention provides products and methods for improving the tolerance of a dough in bakery and patisserie products. More specifically it provides sourdough products obtained through the fermentation of cereals by specific strains of bacteria. The products obtained by using said sourdough products are characterized by having a strengthened dough resulting in bakery and patisserie products with improved physical properties and taste.

BACKGROUND OF THE INVENTION

In the past few decades, the demand for longer shelf-life and consistent quality in baked goods leads to the use of a wide range of additives in the baking industry. These additives, also referred to as bread improvers, include for example emulsifiers, enzymes, soy flour, oxidants and reductants, and are essential for improving dough machinability, reducing resting time and improving baked goods' shelf-life, volume, crust colour, crumb whiteness, aroma and flavour. One important aspect of the baking process is controlling the proofing and the handling of doughs. Indeed, when doughs are over-proofed or when doughs incur shocks during handling, the quality of the baked products can be seriously affected. Therefore the skilled person is constantly searching for ways to improve the "tolerance" of the doughs.

Diacetyl tartaric esters of mono-glycerides (DATEM) are emulsifiers that have been widely used as bread improvers. DATEM improve bread volume and texture as well as dough stability. Lipases have been used over the past two decades to improve some properties of baked goods like dough stability. They hydrolyze triglyceride esters and produce mono- or di-glycerides, glycerol and free fatty acids. Lipases strengthen dough stability and increase bread volume, texture and shelf-life. In the 1990s, the first generation of lipases (e.g. lipase of *Thermomyces lanuginosus*) typically hydrolyze the ester bond between glycerides and fatty acids in positions 1 and 3 triglycerides, producing free fatty acids and mono-glycerides, and producing more polar lipids in the dough. This strengthens the gluten network but overdosing causes stiff doughs, resulting in a decrease in loaf volume. The second generation lipases (e.g. *Fusarium oxysporum* lipase) works on both polar and non-polar lipids in the wheat flour, producing more polar components, such as lysolecithin and digalactosyl monoacyl glycerol (DGMG). Lipases of the third generation increase the expansion of the gluten network and the wall thickness of the crumb cells and decrease the crumb cell density, thereby improving the properties of baked products.

Although lipases and/or phospholipases have already been described to improve dough tolerance, the outcome of their use remains highly unpredictable, due to their different specificities, their different hydrolysis products, their potential synergies or the process conditions or substrates.

Another category of enzymes improving dough tolerance are oxidases. Glucose oxidase is an enzyme with oxidizing effect due to the hydrogen peroxide released from its catalytic reaction. A reinforcement or strengthening of the dough and an improvement of the bread quality can be obtained with the addition of glucose oxidase, although adverse effects are obtained when excessive enzyme levels are added.

The food industry is currently being driven by consumers to become more transparent about the used ingredients. Also, consumers prefer foods without artificial ingredients as foods without artificial ingredients are considered "healthier".

Accordingly, there is still a need for compositions and methods to further improve the properties of baked products such as dough or batter tolerance, or for compositions and methods that avoid the use of ingredients such as chemicals or enzymes.

Sourdough is defined as a dough of flour and water fermented by lactic acid bacteria (LAB) optionally in combination with yeast, used as a leavening agent for the production of bakery products. Usually the flour used for sourdough production and propagation is rye or wheat flour, although other kinds of flour can be used, such as flours of quinoa, semolinas, amaranth, buckwheat or chia. Sourdough was initially obtained from the spontaneous fermentation of microorganisms present in the flour or in other raw material. The spontaneous fermentation (only flour and water) takes nearly one week and at the end the most frequently identified lactic acid bacteria are *Lactobacillus sanfranciscensis*, *Lactobacillus plantarum* and *Weissella ciboria*, in conjunction with the yeasts *Saccharomyces cerevisiae*, *Kazachstania exigua*, and *Candida humilis*.

Compared to products fermented by yeast alone, the sourdough baked goods have a longer shelf life, due to antifungal compounds and bacteriocins production and higher acidity, a higher sensory quality due to increased elasticity, internal humidity, and volatile compound concentration, and a greater nutritional value due to reduction of anti-nutritional compounds such as phytate.

Three types of sourdoughs are generally recognized. Traditional sourdoughs are sourdoughs that are restarted using a part of the previous fermented dough which is therefore constantly renewed in a cyclical way, using specific recipes and ripening conditions. The mother dough is then mixed with rest of the flour, water, salt and fat to a suitable consistency, and then given a short period for fermentation before final proofing and baking. Active sourdoughs are an improved type of sourdoughs using adapted strains or liquid sourdough starters to start the fermentation. These sourdoughs can be pasty or liquid and are generally stable and easy to process for example in an automated bakery. There are enough living lactic acid bacteria and/or yeast to ferment a bread dough successfully or to initiate a multiple stage sourdough process. Finally inactive powder or liquid sourdoughs are used by traditional or industrial bakeries for their convenience since the quality is constant and they are easy to use. These will deliver the acidity and the conventional sourdough flavour directly avoiding a long fermentation step.

It is the aim of the present invention to provide bakery products with improved properties such as dough or batter tolerance, or for compositions and methods that avoid the use of ingredients such as chemicals or enzymes.

SUMMARY OF THE INVENTION

The inventors of the present invention have surprisingly found that it was possible to improve the tolerance of the dough in bakery and of the batter in patisserie products by using a sourdough product based on the fermentation of cereal or cereal fractions fermented by one or more strains of *Clostridium saccharobutylicum*. The sourdough product allows not only to protect the dough against over-proofing or physical shocks but also improves other physical properties (like volume and hardness) as well as the taste of bakery and patisserie products. It further prevents the addition of a large amount of other chemical improving agents or enzymes known for their dough strengthening effect.

It is therefore a first object of the present invention to provide a sourdough product comprising cereal or cereal fractions, wherein said sourdough product is fermented by one or more strains of *Clostridium saccharobutylicum*, in particular said strain of *Clostridium saccharobutylicum* is *Clostridium saccharobutylicum* DSM 13864.

In a particular embodiment the sourdough product as disclosed herein is fermented by one or more additional microorganisms chosen from lactic acid forming bacteria, in particular slow acidifying lactic acid bacteria, and/or yeast strains, in particular said additional microorganism is *Lactobacillus sakei, Lactobacillus crustorum* or *Lactobacillus reuteri*, preferably *Lactobacillus sakei* or *Lactobacillus crustorum*.

In a particular embodiment the sourdough product as disclosed herein is a liquid sourdough product, a paste sourdough product or a dried sourdough product.

In a particular embodiment the sourdough product as disclosed herein is an active or inactive sourdough product.

In a particular embodiment the sourdough product as disclosed herein is a liquid sourdough product characterized by having a pH between 4.2 and 9.0, preferably between 4.2 and 6.0, more preferably between 4.2 and 4.8.

In a particular embodiment the sourdough product as disclosed herein is a dried sourdough product obtained by drying a liquid sourdough product.

In a particular embodiment the sourdough product as disclosed herein further comprises salt in an amount between 10.0 and 25.0% (weight salt/weight sourdough product without salt), preferably between 10.0 and 15.0%.

In a further aspect, the present application relates to methods for obtaining a sourdough product comprising the steps of:
  mixing cereal or cereal fractions with water;
  fermenting the mixture with one or more strains of *Clostridium saccharobutylicum*, at a temperature between 25.0° C. and 50.0° C., preferably between 25.0° C. and 40.0° C., more preferably between 25.0° C. and 35.0° C., even more preferably between 28.0° and 35.0° C. for a period between 8 hours and 1000 hours, preferably between 10 and 100 hours, more preferably between 16 and 72 hours thereby obtaining a liquid sourdough product.

In a particular embodiment the method as disclosed herein further comprises one or more of the following steps:
  inactivating said bacteria;
  adding additional ingredients;
  drying said liquid sourdough product thereby obtaining a dried sourdough product.

In a further aspect, the present application relates to the use of a sourdough product as disclosed herein as an ingredient in the preparation of food products, preferably bakery or patisserie products, in particular as part of an improver, a premix or a complete mix.

In a further aspect, the present application relates to the use of *Clostridium saccharobutylicum* as an ingredient in a sourdough, bakery or patisserie product. In particular said strain of *Clostridium saccharobutylicum* is *Clostridium saccharobutylicum* DSM 13864.

In a further aspect, the present application relates to a baked product comprising a sourdough product as disclosed herein.

DETAILED DESCRIPTION OF THE INVENTION

Before the present method and devices used in the invention are described, it is to be understood that this invention is not limited to particular methods, components, or devices described as such methods, components, and devices may, of course, vary. It is also to be understood that the terminology used herein is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any method and material similar or equivalent to those described herein may be used in practice or testing of the present invention, the preferred methods and materials are now described.

In this specification and the appended claims, the singular forms "a", "an", "the" include both the singular and the plural, unless the context clearly indicates otherwise.

The terms "comprising", "comprises" and "comprised of" as used herein are synonymous with "including", "includes" or "containing", "contains", and are inclusive or open-ended and do not exclude additional, non-recited members, elements or method steps. Where this description refers to a product or process which "comprises" specific features, parts or steps, this refers to the possibility that other features, parts or steps may also be present, but may also refer to embodiments which only contain the listed features, parts or steps. The terms "comprising", "comprises" and "comprised of" also include the term "consisting of".

The enumeration of numeric values by means of ranges of figures comprises all values and fractions in these ranges, as well as the cited end points.

The terms "about" and "approximately" as used when referring to a measurable value, such as a parameter, an amount, a time period, and the like, is intended to include variations of +/10% or less, preferably +/−5% or less, more preferably +/−1% or less, and still more preferably +/−0.1% or less, of and from the specified value, in so far as the variations apply to the invention disclosed herein. It should be understood that the value to which the term "about" or "approximately" refers per se has also been disclosed.

The inventors of the present invention have surprisingly found that it was possible to improve the tolerance of the dough in bakery and of the batter in patisserie products by using a sourdough product based on the fermentation of cereal or cereal fractions fermented by one or more strains of *Clostridium saccharobutylicum*. The sourdough product allows not only to protect the dough against over-proofing or physical shocks but also improves other physical properties (like volume and hardness) as well as the taste of bakery and patisserie products. It further prevents the addition of a large amount of other chemical improving agents or enzymes known for their dough strengthening effect.

In the present context the dough tolerance refers to the capacity of a dough or a batter, preferably a bakery dough, to maintain its shape in stress conditions such as a prolonged proofing time or mechanical shocks during or after proofing and to provide, after baking, a baked product with properties (e.g. volume) comparable to a baked product obtained with an unstressed dough or batter.

Other physical properties are advantageously improved by the use of the sourdough of the present invention. Depending of the type of desired baked product such improved properties may be increased volume, reduced hardness, increased cohesiveness, increased resilience, increased springiness, reduced stickiness, reduced adhesiveness, reduced gumminess and/or reduced chewiness. Preferably the improved properties are increased volume, reduced hardness and improved elasticity.

It is therefore a first object of the present invention to provide sourdough products that improve the tolerance of the doughs and the batters and improve other physical properties and taste of bakery and patisserie products. The sourdough products as disclosed herein are characterized in that the sourdough products comprise cereal(s) or cereal fraction(s), wherein said sourdough product is fermented by one or more strains of *Clostridium saccharobutylicum*.

In particular the cereal(s) or cereal fraction(s) are fermented by one or more strains of *Clostridium saccharobutylicum.*

In a particular embodiment the strain of *Clostridium saccharobutylicum* is *Clostridium saccharobutylicum* DSM 13864.

The term "cereal", in the context of the present invention, refers to the edible components of plants of the botanical family of the Poaceae, including but not limited to species such as wheat, barley, oat, spelt, rye, sorghum, maize, triticale, millet, teff and/or rice. Preferably, the cereals are chosen among the group of wheat, maize (corn), rice or rye. More preferred cereals are rye, rice and wheat. An even more preferred cereal is wheat.

The term "cereal fraction", in the context of the present invention, refers to all or part of the fractions resulting from mechanical reduction of the size of grains, through, as examples but not limited to, cutting, rolling, crushing, breakage or milling, with or without fractionation, through, as examples but not limited to, sieving, screening, sifting, blowing, aspirating, centrifugal sifting, wind sifting, electrostatic separation, or electric field separation. Preferred cereal fractions are flours, whole flours, brans and/or any combination thereof.

*Clostridium saccharobutylicum* is an obligately anaerobic spore-forming bacterium and one of four distinct species of solvent-producing clostridia capable of fermenting various carbohydrates to produce acetone and butanol. Clostridia are a large class of microorganisms that were traditionally grouped together based on the characteristic "look" of the family of cells. When examined under a microscope, these bacterial cells are rod (or 'spindle') shaped. Clostridia can be found in soil, water, sewage, or even in human and animal intestines. A description of *Clostridium saccharobutylicum* can be found in Keis S. et al (International Journal of Systematic and Evolutionary Microbiology (2001), 51, p. 2095-2103). The type strain of this species is *Clostridium saccharobutylicum* DSM 13864 and has been isolated from soybean in the Unites States.

Strains of *Clostridium saccharobutylicum* may also advantageously identified/characterized by their DGGE (Denaturing Gradient Gel Electrophoresis) profile.

In a particular embodiment the sourdough product as disclosed herein is characterized in that said sourdough product is fermented by *Clostridium saccharobutylicum*, in particular *Clostridium saccharobutylicum* DSM 13864 and one or more additional microorganisms chosen from lactic acid forming bacteria and/or yeast strains. More in particular the one or more strains of lactic acid bacteria are chosen from slow acidifying lactic acid bacteria. According to the present invention a slow acidifying bacteria is a bacteria that does not cause a drop of pH below 4.8 during the first 12 hours of a sourdough fermentation and that produces sourdough at the end of fermentation with a pH above 4.2. Even more preferably the one or more strains of lactic acid bacteria are strains of *Lactobacillus*, preferably selected from the group of *Lactobacillus sakei, Lactobacillus crustorum* and *Lactobacillus reuteri*. In particular said additional microorganism is *Lactobacillus sakei* or *Lactobacillus crustorum.*

In a particular embodiment the sourdough product as disclosed herein is characterized in that said sourdough product is a liquid sourdough product, a paste sourdough product or a dried sourdough product.

The sourdough products as disclosed herein may be provided in many forms. Liquid sourdough products are the most commonly used type. However, also other types of sourdough products are available, including paste, dried or dry sourdough products. Sourdough products under a dry form are typically obtained by drying a liquid sourdough product. Preferably, the dry matter of the solid/powdered composition is more than 85% (w/w), preferably more than 90%, and more preferably 92% or more. Said range thus also provides 86, 87, 88, 89, 90, 91, 92, 93, 94, 95, 96, 97, 98, 99 or 100% dry matter. In a particular embodiment the sourdough product as disclosed herein is a dried sourdough product obtained by drying a liquid sourdough product.

The drying of the liquid sourdough product can be performed using the typical drying techniques available to the skilled person. Preferably the dried sourdough product is obtained through spray-drying of the liquid sourdough product. Preferably, the dry matter of the solid/powdered composition is more than 85%, preferably more than 90%, more preferably 92% or more. This range includes the dry matter values of 86, 87, 88, 89, 90, 91, 92, 93, 94, 95, 96, 97, 98, 99 and 100%.

According to a particular embodiment, the sourdough product as disclosed herein is a liquid sourdough product wherein said liquid sourdough product is characterized by having a dry matter between 5% (w/w) and 50%, preferably between 10% and 40%, more preferably between 10% and 35%. Said range thus also provides any of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 and 49% dry matter.

The liquid sourdough product as disclosed herein may be characterized by its pH. Preferably the pH of the liquid sourdough is between 4.2 and 9.0, more preferably between 4.2 and 6.0, even more preferably between 4.2 and 4.8.

According to a particular embodiment, the sourdough product as disclosed herein is an active or inactive sourdough product. The sourdough product according to the present invention may be an active sourdough product. By this is meant that the sourdough product contains active and/or viable microorganisms. An active sourdough product can be used as a starter to produce pasty or other sourdough products having the same specifications and properties as described above. Like conventional active sourdoughs the active liquid sourdough product guarantees a homogeneity in quality and in processing.

More particularly, the present invention provides in liquid sourdough products wherein said liquid sourdough product is an active or an inactive liquid sourdough product. Alternatively, the invention provides in dried sourdough products which may be active or inactive dried sourdough products.

According to a particular embodiment, the sourdough product as disclosed herein further comprises additional ingredients such as, but not limited to, yeast, yeast extract, salt(s), sugar(s), oxidant(s), reducer(s), enzyme(s), protein(s), fat(s) and combinations thereof. Preferred additional ingredients are yeast(s) and/or salt(s).

According to a particular embodiment, the sourdough product as disclosed herein further comprises salt (e.g. NaCl) in an amount between 10.0 and 25.0% (weight salt/weight sourdough product without salt), preferably between 10.0 and 15.0%.

In a further aspect, the present application relates to methods to obtain the compositions or the sourdough products as described herein and in particular a method for obtaining a sourdough product comprising the steps of:
  mixing cereal or cereal fractions with water;
  fermenting the mixture with one or more strains of *Clostridium saccharobutylicum*, in particular *Clostridium saccharobutylicum* DSM 13864, at a temperature between 25.0° C. and 50.0° C., preferably between 25.0° C. and 40.0° C., more preferably between 25.0° C. and 35.0° C., even more preferably between 28.0° and 35.0° C. for a period between 8 hours and 1000 hours, preferably between 10 and 100 hours, more preferably between 16 and 72 hours thereby obtaining a liquid sourdough product.

In a particular embodiment the method as disclosed herein is characterized in that said sourdough product is fermented by *Clostridium saccharobutylicum*, in particular *Clostridium saccharobutylicum* DSM 13864, and one or more additional microorganisms chosen from lactic acid forming bacteria and/or yeast strains. More in particular the one or more strains of lactic acid bacteria are chosen from slow acidifying lactic acid bacteria. Even more preferably the one or more strains of lactic acid bacteria are strains of *Lactobacillus*, preferably selected from the group of *Lactobacillus sakei, Lactobacillus crustorum* and *Lactobacillus reuteri*. In particular said additional microorganism is *Lactobacillus sakei* or *Lactobacillus crustorum.*

In the method as disclosed herein the cereals and/or cereal fractions are firstly suspended in a suitable liquid, preferably water, thereby obtaining a (liquid) mixture. The dry matter of this (liquid) mixture is preferably between 35 and 75% (w/w).

Said (liquid) mixture is fermented by the addition of living cells comprising, or consisting of, *Clostridium saccharobutylicum*, in particular *Clostridium saccharobutylicum* DSM 13864, or of *Clostridium saccharobutylicum*, in particular *Clostridium saccharobutylicum* DSM 13864, and one or more additional microorganisms chosen from lactic acid forming bacteria and/or yeast strains, preferably in an amount between $10^5$ to $10^9$ cells/g of (liquid) mixture. The fermentation/incubation is performed for a period between 8 and 1000 hours, preferably between 10 and 100 hours, more preferably between 16 and 72 h and at a temperature between 25 and 40° C., preferably between 25° C. and 35° C., more preferably between 28° C. and 35° C. This range includes temperatures of 29° C., 30° C., 31° C., 32° C., 33° C., 34° C. and 35° C.

In a preferred embodiment the living cells are added under the form of cells having been first cultivated in another culture medium to obtain a starter culture. When two or more bacterial species are used the strains are preferably separately cultivated in another culture medium to obtain a starter culture.

In a particular embodiment of the method as disclosed herein the culture is performed without agitation or aeration (or in the absence of air/oxygen addition to the culture).

According to a particular embodiment, the method as disclosed herein provides in a liquid sourdough product, being the end product of the fermentation step, characterized by having a pH between 4.2 and 9.0, preferably between 4.2 and 6.0, more preferably between 4.2 and 4.8. In some embodiments suitable compounds known to the skilled person may be used to adjust the pH to the desired value.

In a particular embodiment, in the method as disclosed herein the pH during the first 12 hours of fermentation is preferably (maintained) above 4.8.

According to a particular embodiment, the method as disclosed herein provides in a sourdough product, the end product of the fermentation step, characterized by a dry matter at the end of the fermentation is comprised between 25% and 75% (w/w), preferably between 35% and 75%, more preferably between 50% and 75%, as defined above.

According to a particular embodiment, the method as disclosed herein provides in a two-step fermentation system. Accordingly, the strain of *Clostridium saccharobutylicum* is pre-fermented in a first step in a fermentation medium without the cereal or cereal fraction and then used as an active starter for a second fermentation step containing the cereal or the cereal fraction and optionally the lactic acid bacteria.

In another embodiment a two-step fermentation system can be used wherein *Clostridium saccharobutylicum* is first added to the cereal or cereal fraction and the lactic acid bacteria is added about 20 hours after the beginning of the fermentation.

In a particular embodiment, the method as provided herein further comprises one or more of the following steps:

inactivating said bacteria;

adding additional ingredients;

drying said liquid sourdough product thereby obtaining a dried sourdough product.

As referred to herein, the inactivation of the bacteria, may be performed using conventional methods known in the art such as, but not limited to, heat inactivation or salt inactivation. A suitable preferred example of inactivation is the addition of salt, preferably NaCl, at a concentration between 10.0% and 25.0% (weight of salt/weight of liquid sourdough), preferably between 10.0% and 15.0%.

In the case of a dry sourdough product the inactivation step may be omitted.

In a particular embodiment of the method as disclosed herein the additional ingredients added to the sourdough product may be chosen from the non-limiting list of yeast, yeast extract, salt(s), sugar(s), oxidant(s), reducer(s), enzyme(s), protein(s), fat(s) and combinations thereof. Preferred additional ingredients are yeast(s) and/or salt(s). Preferably the additional ingredient is the salt that is used for inactivating the bacteria. The additional ingredients may be added before or after the optional drying step.

In a particular embodiment of the method as disclosed herein the drying of the liquid sourdough product may be performed using the typical drying techniques available to the skilled person. Preferably the liquid sourdough product is dried through spray-drying. Preferably, at the end of the drying step, the dry matter of the solid/powdered composition is more than 85%, preferably more than 90%, more preferably 92% or more. This range includes the dry matter values of 86, 87, 88, 89, 90, 91, 92, 93, 94, 95, 96, 97, 98, 99 and 100%.

In a further embodiment the present application provides in methods to improve the tolerance of bakery doughs or patisserie batters that comprise the steps of:
preparing a sourdough product as described herein;
adding said sourdough to a dough or batter; and;
optionally adding a phospholipase to the dough or batter.

The methods as disclosed herein improve in particular (the quality of) bakery products and patisserie products, preferably bakery products. More particularly, the methods as disclosed herein improve the tolerance of bakery doughs and patisserie batters.

In a further embodiment the present application provides in methods to improve the characteristics of baked products that comprise the steps of:
preparing a sourdough product as described herein;
adding said sourdough to a dough or batter
optionally adding a phospholipase to the dough or batter; and;
preparing a baked product by baking said dough or batter.

Advantageously the compositions as disclosed herein also further improve physical properties of the baked products such as the volume, the softness, the cohesiveness, the resilience, the springiness, the stickiness, the adhesiveness, the gumminess and the chewiness. Preferably the baked products have an improved volume and/or a reduced hardness and/or an improved elasticity.

In a further aspect, the present application relates to the use of a sourdough product as disclosed herein as an ingredient in the preparation of food products, preferably bakery or patisserie products, in particular as part of an improver, a premix or a complete mix.

An "improver" as used herein refers to a composition of the invention further comprising ingredients and/or technological aids used for their beneficial properties during the preparation of baked products and/or after baking. These properties comprise but are not limited to aspect, volume, freshness, conservation, color, structure or short bite of the baked products.

The term "premix" as used herein refers typically to an improver composition wherein the concentration in "active" component is lower than in a bakery improver. Typically a premix is used at a higher dose than an improver (weight/weight of flour).

The term "complete mix" as used herein refers typically to a composition comprising all the ingredients needed to prepare a dough that can be baked to obtain a baked product, generally with the exception of water. In particular when the leavening agent is a biological agent, more particularly baking yeast, it can also be excluded from the complete mix. A complete mix according to the present invention comprises the sourdough product according to the invention and all the ingredients needed to prepare a dough that can be baked to obtain a baked product.

It is a further object of the present application to provide the use of a sourdough product, an improver, a mix or a complete mix according to the invention for preparing a bakery or a patisserie product. The inventors have indeed found that the use of a particular strain as starter for a sourdough as disclosed herein, in bakery or patisserie applications has an improved effect on dough or batter tolerance.

In a further aspect, the present application relates to the use of Clostridium saccharobutylicum as an ingredient in a sourdough, bakery or patisserie product.

The compositions as disclosed herein improve particularly (the quality of) bakery products and patisserie products, preferably bakery products. More particularly, the compositions as disclosed herein improve the tolerance of bakery doughs and patisserie batters. Advantageously the compositions as disclosed herein also further improve physical properties of the baked products such as the volume, the softness, the cohesiveness, the resilience, the springiness, the stickiness, the adhesiveness, the gumminess and the chewiness. Preferably said composition improves the volume (increased volume), the softness (reduced hardness) and/or elasticity.

In a further aspect, the present application relates to a baked product comprising a sourdough product as disclosed herein. In particular the baked product is prepared from a dough or batter comprising the composition as disclosed herein.

In the present context a baked product is a bakery or patisserie product known in the art, such as for instance those selected from the group comprising bread, soft rolls, bagels, donuts, Danish pastry, hamburger rolls, pizza, pita bread, ciabatta, sponge cakes, cream cakes, pound cakes, muffins, cupcakes, steamed cakes, waffles, brownies, cake donuts, yeast raised donuts, baguettes, rolls, crackers, cookies, pie crusts, rusks and/or other baked products. More in particular the baked product is bread, baguettes and/or rolls.

In a further aspect, the present application relates to the use of a sourdough product as disclosed herein for improving the dough tolerance of a dough or a batter product, preferably a bakery dough or batter product. In the present context the dough tolerance refers to the capacity of a dough or a batter, preferably a bakery dough, to maintain its shape in stress conditions such as a prolonged proofing time or mechanical shocks during or after proofing and to provide, after baking, a baked product with properties (e.g. volume) comparable to a baked product obtained with an unstressed dough or batter.

In a further aspect, the present application relates to a method for improving the dough tolerance of a dough or a batter product, preferably a bakery dough or batter product, comprising the step of adding a sourdough product as disclosed herein during the preparation of food products, preferably bakery or patisserie products. In particular, said sourdough product is added as an ingredient during the preparation of food products, preferably bakery or patisserie products, preferably as part of an improver, a premix or a complete mix.

EXAMPLES

Example 1: Strains and Media

Strains:
Clostridium saccharobutylicum DSM 13864 was obtained from DSMZ (Leibniz-Institut—Deutsche Sammlung von Mikroorganismen and Zellkulturen GmbH, Germany)
Clostridium butyricum LMG 1212 was obtained from LMG (BCCM/LMG Bacterial Collection (Belgian Co-ordinated collections of micro-organisms)—Laboratory of Microbiology; University of Genth; Belgium)

*Lactobacillus sakei* LMG 9486 was obtained from LMG (BCCM/LMG Bacterial Collection (Belgian Co-ordinated collections of micro-organisms)—Laboratory of Microbiology; University of Genth; Belgium).

*Lactobacillus crustorum* LMG P-29154 was obtained from LMG (BCCM/LMG Bacterial Collection (Belgian Co-ordinated collections of micro-organisms)—Laboratory of Microbiology; University of Genth; Belgium).

*Leuconostoc citreum* was isolated from sourdough.

Media:
RCM (Reinforced Clostridium medium): 10 g/l meat extract, 5 g/l pepton, 3 g/l yeast extract, 1 g/l starch, 5 g/l NaCl, 3 g/l Na-acetate, 5 g/l glucose
MRS: 10 g/l pepton, 8 g/l meat extract, 4 g/l yeast extract, 20 g/l glucose, 1 g/l Tween 80, 2 g/l $K_2HPO_4$, 5 g/l Na-acetate.$3H_2O$, 2 g/l triammonium citrate, 0.2 g/l $MgSO_4.7H_2O$, 0.05 g/l $MnSO_4.4H_2O$, pH 6.5

Starter Cultures

Bacterial strains were incubated in RCM (for *Clostridium* strains) or MRS (for *L. sakei, L. crustorum* and *L. citreum*) respectively for 48 h-72 h and 24 h at 30° C. without agitation (microaerophilic conditions). CFU/ml (colony forming units) were obtained by serial dilution in physiological water (0.9% NaCl) and plating on agar plates. 2 dilutions were counted and the average was calculated.

Example 2: Effect on Bread Dough Tolerance of a Sourdough Product with *Clostridium saccharobutylicum*

Sourdough

A sourdough product (Sourdough product A) was prepared by mixing 1000 g wheat flour (Pur 8, Ceres, Belgium) and 1000 g water in a recipient. *Clostridium saccharobutylicum* DSMZ 13864 was inoculated at a concentration of $10^6$ CFU/g of mixture and the mixture was fermented during 24 h at 30° C. without any agitation. After fermentation the sourdough had a pH of 4.92.

Breads

Breads were prepared using the ingredients of Table 1. 2 tests were included with ingredients known for their effect on dough tolerance products. The first control test was based on the addition of an emulsifier (MD HP20, Puratos, Belgium) and the second test was based on the addition of an enzyme (Lipopan Xtra BG, Novozymes, Denmark). Lipopan Xtra BG is a lipase that shows a positive effect on dough tolerance.

TABLE 1

| Recipe | Reference 1 | HP20 | Lipopan Xtra BG | Test 1 | Test 2 |
|---|---|---|---|---|---|
| Flour (Crousti flour, Dossche Mills, Deinze, Belgium) | 2600 | 2600 | 2600 | 2470** | 2470** |
| $H_2O$ | 1482 | 1482 | 1482 | 1352** | 1325** |
| Yeast | 130 | 130 | 130 | 130 | 130 |
| Salt | 44.2 | 44.2 | 44.2 | 44.2 | 44.2 |
| Improver* | 39 | 39 | 39 | 39 | 39 |
| Emulsifier (MD HP20, Puratos, Belgium) | | 7.8 | | | |
| Lipopan Xtra BG (Novozymes, Denmark) | | | 0.3975 | | 0.3975 |
| Sourdough product A | | | | 260 | 260 |

*contains ascorbic acid and enzymes

**The sourdough product was added based on flour replacement. This means that the quantity of flour and of water present in the sourdough product are subtracted from the quantity of flour and water of the reference recipe.

The ingredients were mixed for 2 min at low and 6 min at high speed in a Diosna SP24 mixer. The final dough temperature was 29° C. The doughs were moulded manually (600 g dough pieces) and underwent an intermediate proof at 21° C. for 20 min at 50-55% relative humidity in the Bakery lab. 600 g dough pieces were made up using the on the line Quality & Ethics—Jac Unic set at R6/L16 and moulded. The dough pieces without shock obtained a final proof at 35° C. for 50 min at 95% relative humidity in a Koma SunRiser. The dough pieces with shock had a final proof at 35° C. for 70 min at 95% relative humidity in a Koma SunRiser. These doughs received a shock by letting the baking pans fall from a height of 5.5 cm. Then the breads were baked at 230° C. during 35 min in a Miwe Condo Oven 2 (Michael Wenz-Arnstein—Germany) with steam (0.1 L before and 0.2 L after ovening of the breads). The breads were cooled down during 180 min before the volume was measured.

Bread Analysis

The volume of the breads was measured using the commonly used rapeseed displacement method. Average volume of four breads was determined. The results are given in Table 2.

TABLE 2

| | Without shock | With shock |
|---|---|---|
| Reference 1 | 2200 | 1925 |
| HP20 | 2950 | 3250 |
| Lipopan Xtra BG | 2725 | 2550 |
| Test 1 | 2600 | 3200 |
| Test 2 | 3275 | 3750 |

The use of a sourdough product fermented with *Cl. saccharobutylicum* shows a positive effect on dough tolerance. The use of a combination of the sourdough product and a lipase shows an even better effect on dough tolerance.

Example 3: Other *Clostridium* Species

Sourdoughs

Sourdough products were prepared as in example 2 but under sterile conditions with heat treated flour (Flamingo, Meneba, The Netherlands) and sterile water. The sourdough products were inoculated with *Clostridium saccharobutylicum* DSMZ 13864 (Sourdough product B) or with another strain belonging to the *Clostridium* family, *Clostridium butyricum* LMG 1212 (Sourdough product C) at a concentration of $10^6$ CFU/g of sourdough and incubated during 24 h at 30° C. After fermentation Sourdough product B had a pH of 4.9 and Sourdough product C had a pH of 5.06.

Breads

Breads were prepared as in example 2 with the same recipe for the reference and the same recipe as in Test 1 with either 260 g of Sourdough product B for Test 3 or 260 g Sourdough product C for Test 4.

The breads were analyzed as in example 2. The results are given in table 3.

TABLE 3

| | Without test | With test |
|---|---|---|
| Reference 2 | 2650 | 2200 |
| Test 3 | 2525 | 2950 |
| Test 4 | 2725 | 2150 |

Only the use of a sourdough product fermented with *Cl. saccharobutylicum* shows a positive effect on dough tolerance.

Example 4: Combination with Lactic Acid Bacteria

Different lactic acid bacteria were used in combination with *Clostridium saccharobutylicum* as starter for the sourdough. Starter cultures of *Lactobacillus sakei* LMG 9486, *Lactobacillus crustorum* LMG P-29154 (slow acidifying lactic acid bacteria) and *Leuconostoc citreum* (isolated from sourdough) (fast acidifying lactic acid bacteria) were obtained by inoculating a single colony of each strain in MRS medium. The cultures were incubated during 24 h at 30° C. without agitation (microaerophilic conditions).

Sourdough products were prepared with 1000 g wheat flour (Ceres, Belgium), 1000 g tap water and the corresponding starter cultures ($10^6$ CFU/g for the *Clostridium* strain and $10^7$ CFU/g for the *Lactobacillus* or the *Leuconostoc* strains). Sourdough product D was fermented with *Cl. saccharobutylicum* as a starter culture, Sourdough product E was fermented with a mixture of *Cl. saccharobutylicum* and *L. crustorum* starter cultures, Sourdough product F was fermented with a mixture of *Cl. saccharobutylicum* and *L. sakei* starter cultures and Sourdough G was fermented with a mixture of *Cl. saccharobutylicum* and *Lc. citreum*. The mixture was mixed and incubated at 30° C. during 20 h without shaking.

TABLE 4

| Final pH of the sourdoughs: | |
| --- | --- |
| | pH |
| Sourdough product D : Cl. saccharobutylicum | 4.75 |
| Sourdough product E : Cl. saccharobutylicum and L. crustorum | 4.22 |
| Sourdough product F : Cl. saccharobutylicum and L. sakei | 4.55 |
| Sourdough product G : Cl. saccharobutylicum and Lc. citreum | 3.86 |

Breads

Breads were prepared as in example 2 with the same recipe for the reference and the same recipe as in Test 1 with either 260 g of Sourdough product D for Test 5, 260 g Sourdough product E for Test 6, 260 g of Sourdough F product for Test 7 or 260 g of Sourdough product G for Test 8.

The breads were analyzed as in example 2. The results are given in table 5. The volume of the breads are relative to the reference that has been set to 100.

TABLE 5

| | With shock |
| --- | --- |
| Reference 3 | 100 |
| Test 5 | 126 |
| Test 6 | 123 |
| Test 7 | 141 |
| Test 8 | 82 |

A sourdough inoculated with *Cl. saccharobutylicum* can be combined with a slow acidifying lactic acid bacteria like *L. crustorum* and *L. sakei* without any loss on dough tolerance. On the contrary combination with a fast acidifying lactic acid bacteria like *L. citreum* resulted in a loss of dough tolerance.

Example 5: Effect on Other Characteristics of the Bread 130 g (Test 9) and 260 g (Test 10) of Sourdough product F of example 4 were used to prepare breads as in example 2.

The softness of the breads was measured with a TA-XT2 texture analyzer (Stable Micro Systems UK). The bread was sliced and the force to obtain a 25% deformation of 4 slices of 1 cm was measured. This force is called the hardness. The hardness is measured at day 1 and at day 7 after baking. The difference between the two measured forces is "the loss of softness" (Loss of softness=deformation force at day 7−deformation force at day 1)

It is a relative measure. The absolute values have no meaning as such but should be compared to a reference for interpretation.

The elasticity is the difference between the aforementioned force and the force after 20 sec of relaxation. When the elasticity is lower than in the reference bread, this means that the crumb is less resilient. The crumb, when compressed does not regain its original shape. This means that during slicing or handling the crumb structure may be lost irreversibly.

The results are presented in table 6

TABLE 6

| | hardness | | elasticity | |
| --- | --- | --- | --- | --- |
| | day 1 | day 7 | day 1 | day 7 |
| Reference 4 | 245 | 592 | 69 | 53 |
| Test 9 | 124 | 354 | 69 | 58 |
| Test 10 | 116 | 343 | 68 | 55 |

The addition of sourdough fermented with *Cl. saccharobutylicum* and *L. sakei* gives an effect on bread hardness and elasticity in comparison with the reference.

Example 6: Effect of Sourdough on the Characteristics of Cream Cake

Cream cakes were prepared using the following basic recipe and process (reference 5).

Recipe: Mix Satin Crème Cake (Puratos, Belgium): 1000 g
Eggs: 350 g
Oil: 300 g
Water: 225 g
Method: Mixer: Hobart
Instrument: Paddle
Speed: 1 min speed 1 and 2 min speed 2
Adding oil and water, 1 min speed 1, scrape down and 2 min speed 1
Batter weight: 300 g
Temperature: 180° C.
Time: 45 min Cakes of Test 11 were obtained by adding 50 of sourdough product F of example 4 to the basic recipe.

The volume of the cakes was measured using the commonly used rapeseed displacement method. Average volume of four cakes was determined.

The hardness (as opposite of softness), the cohesiveness, the resilience, the springiness, the stickiness, the gumminess and the chewiness of the cake crumb were evaluated by performing a Texture Profile Analysis (TPA) on cake crumb samples with a Texture Analyzer (TAXT2, Stable Micro Systems, UK). Two consecutive deformations of a cylindrical cake crumb sample (diameter=45 mm, height 40 mm) with a cylindrical probe (diameter=100 mm) with a maximum deformation of 50% of the initial height of the product were performed at a deformation speed of 2 mm/sec and a waiting time between the two consecutive deformations of 3 sec. Force, measured by the load cell of the Texture Analyzer, was recorded as a function of time.

The hardness is the maximum force needed to apply a fixed deformation of 50% of the initial height of the cake sample.

The cohesiveness is calculated as the ratio (expressed in percent) between the surface under the second deformation curve (downwards+upwards) and the ratio under the first deformation curve (downwards+upwards).

The resilience is calculated as the ratio (in %) between the surface under the first deformation curve when the probe is moving upwards to the surface under the first deformation curve when the probe is moving downwards.

The stickiness is the negative force needed to loosen the probe from the cake surface after the deformation.

The gumminess is calculated as the mathematical product of hardness and the cohesiveness.

The chewiness is calculated as the mathematical product of the hardness, the cohesiveness and the springiness.

|  | Reference 5 | Test 11 |
| --- | --- | --- |
| Volume | 1250 | 1325 |
| Hardness | 1567 | 1298 |
| Cohesiveness | 56.43 | 57.62 |
| Resilience | 21.41 | 21.43 |
| Stickiness | −24 | −3 |
| Gumminess | 884 | 747 |
| Chewiness | 724 | 603 |

Conclusion: The use of a sourdough fermented with *Cl. saccharobutylicum* and *L. sakei* during the preparation of cream cakes resulted mainly in an increase in volume and a decrease in hardness, gumminess and chewiness of the cakes. The other parameters were comparable to the reference.

The invention claimed is:

1. A sourdough product comprising cereal or cereal fractions inoculated with one or more strains of *Clostridium saccharobutylicum*, wherein said sourdough product is the product of fermentation of the cereal or cereal fractions by said one or more strains of *Clostridium saccharobutylicum*.

2. The sourdough product according to claim 1, wherein said strain of *Clostridium saccharobutylicum* is *Clostridium saccharobutylicum* DSM 13864.

3. The sourdough product according to claim 1, wherein said sourdough product is fermented by one or more additional microorganisms chosen from lactic acid forming bacteria and yeast strains.

4. The sourdough product according to claim 3, wherein said additional microorganism is *Lactobacillus sakei, Lactobacillus crustorum* or *Lactobacillus reuteri*.

5. The sourdough product according to claim 1, wherein said sourdough product is a liquid sourdough product, a paste sourdough product or a dried sourdough product.

6. The sourdough product according to claim 1, wherein said sourdough product is an active or inactive sourdough product.

7. The sourdough product according to claim 1, wherein said sourdough product is a liquid sourdough product characterized by having a pH between 4.2 and 9.0.

8. The sourdough product according to claim 1, wherein said sourdough product is a dried sourdough product obtained by drying a liquid sourdough product.

9. The sourdough product according to claim 1, further comprising salt in an amount between 10.0 and 25.0% (weight salt/weight sourdough product without salt).

10. A method for obtaining a sourdough product comprising the steps of:
   mixing cereal or cereal fractions with water;
   adding one or more strains of *Clostridium saccharobutylicum*, and fermenting the mixture at a temperature between 25.0° C. and 50.0° C. for a period between 8 hours and 1000 hours thereby obtaining a liquid sourdough product.

11. The method according to claim 10, wherein the method further comprises one or more of the following steps:
   inactivating said bacteria;
   adding additional ingredients;
   drying said liquid sourdough product thereby obtaining a dried sourdough product.

12. An ingredient in the preparation of food products as part of an improver, a premix or a complete mix comprising the sourdough product of claim 1.

13. An ingredient in a sourdough, bakery or patisserie product wherein a *Clostridium saccharobutylicum* strain is added to the ingredient.

14. The ingredient according to claim 13, wherein said strain of *Clostridium saccharobutylicum* is *Clostridium saccharobutylicum* DSM 13864.

15. A baked product comprising a sourdough product according to claim 1.

16. A method for improving the dough tolerance of a dough or a batter product comprising the step of adding a sourdough product according to claim 1 during the preparation of the dough or batter product.

17. The method according to claim 16, wherein said sourdough product is part of an improver, a premix or a complete mix.

18. The sourdough product according to claim 3, wherein said lactic acid forming bacteria are slow acidifying lactic acid bacteria.

19. The sourdough product according to claim 7, wherein said liquid sourdough product is characterized by having a pH between 4.2 and 6.0.

20. The sourdough product according to claim 7, wherein said liquid sourdough product is characterized by having a pH between 4.2 and 4.8.

21. The sourdough product according to claim 1 further comprising salt in an amount between 10.0 and 15.0% (weight salt/weight sourdough product without salt).

22. The method for obtaining a sourdough product according to claim 10, wherein the mixture is fermented at a temperature between 25.0° C. and 40.0° C.

23. The method for obtaining a sourdough product according to claim 10, wherein the mixture is fermented at a temperature between 28.0° and 35.0° C.

24. The method for obtaining a sourdough product according to claim 10, wherein the mixture is fermented for a period between 10 and 100 hours.

25. The method for obtaining a sourdough product according to claim 10, wherein the mixture is fermented for a period between 16 and 72 hours.

26. The ingredient in the preparation of food products according to claim 12, wherein said food products are bakery or patisserie products.

27. The method according to claim 16, wherein said dough or batter product is a bakery dough or batter product.

28. The method according to claim 16, wherein said dough or batter product is a bakery or patisserie product.

\* \* \* \* \*